United States Patent

Ovalles et al.

Patent Number: 5,321,187
Date of Patent: Jun. 14, 1994

[54] CATALYST FOR THE DIRECT CONVERSION OF METHANE TO HIGHER HYDROCARBONS AND METHOD FOR THE PREPARATION OF SAME

[75] Inventors: Cesar Ovalles; Nora Urbano; Francisco Rosa, all of Caracas, Venezuela

[73] Assignee: Intevep, S.A., Caracas, Venezuela

[21] Appl. No.: 8,623

[22] Filed: Jan. 25, 1993

Related U.S. Application Data

[62] Division of Ser. No. 846,626, Mar. 5, 1992, Pat. No. 5,212,139.

[51] Int. Cl.$^5$ .............................................. C07C 2/00
[52] U.S. Cl. .................... 585/500; 585/654; 585/656; 585/658; 585/661; 585/943; 585/700
[58] Field of Search ............... 585/500, 454, 656, 658, 585/661, 943, 700

[56] References Cited

U.S. PATENT DOCUMENTS

| | | | |
|---|---|---|---|
| 4,499,322 | 2/1985 | Jones et al. | 585/943 |
| 4,547,610 | 10/1985 | Sofranko et al. | 585/943 |
| 4,613,718 | 9/1986 | Jaecker et al. | 585/943 |
| 4,634,800 | 1/1987 | Withers, Jr. et al. | 585/943 |
| 4,650,781 | 3/1987 | Jones et al. | 585/943 |

Primary Examiner—Patrick P. Garvin
Assistant Examiner—E. D. Irzinski
Attorney, Agent, or Firm—Bachman & LaPointe

[57] ABSTRACT

A method for preparing a catalyst for conversion of methane to higher hydrocarbons, discloses the steps of: forming a mixture of a manganese aqueous solution and an oxidative agent aqueous solution in an inorganic oxide support material; varying a pH value of the mixture between acidic and basic values to obtain a precipitate of manganese oxide; drying the manganese oxide precipitate; impregnating the dried manganese oxide precipitate with a promoter to obtain an impregnated solid; drying the impregnated solid; and calcining the impregnated solid until a surface atomic ratio of promoter to manganese is at least 5. The catalyst so acquired may be contacted with a methane gas to obtain stable conversion values over extended reaction times.

5 Claims, 2 Drawing Sheets

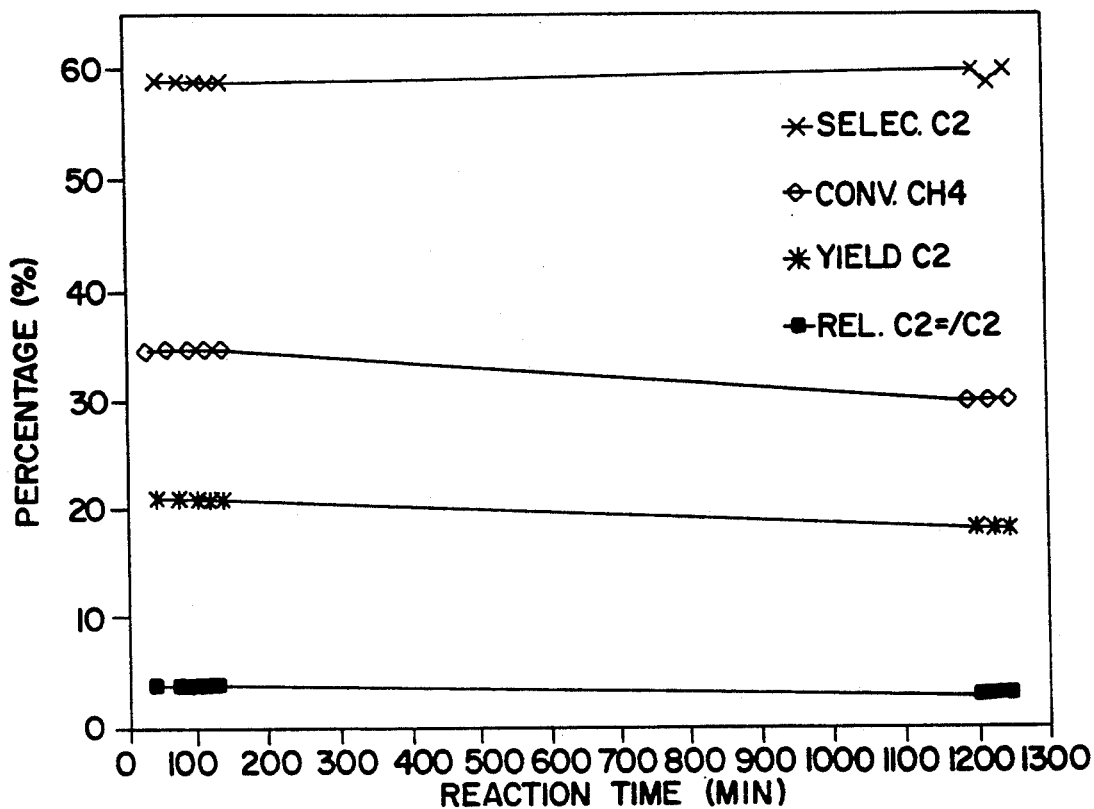
FIG. 3
FIG. 4
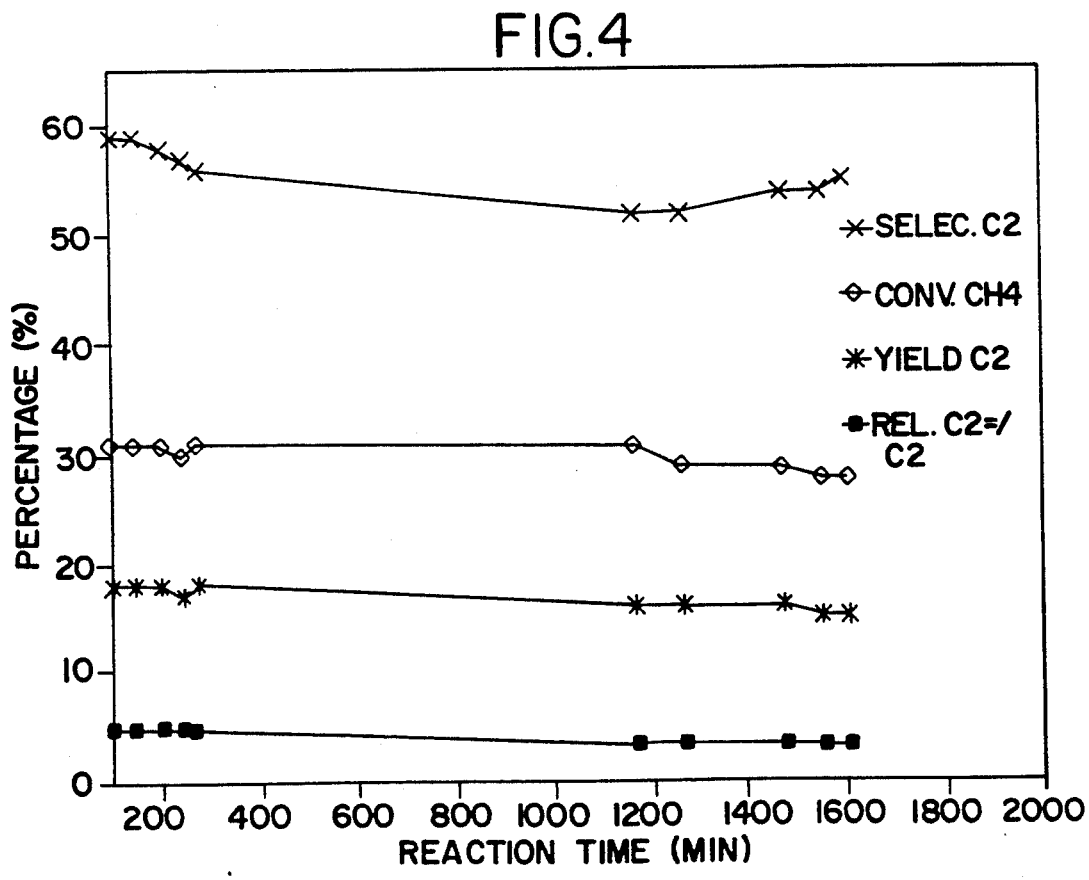

CATALYST FOR THE DIRECT CONVERSION OF METHANE TO HIGHER HYDROCARBONS AND METHOD FOR THE PREPARATION OF SAME

This is a Division, of application Ser. No. 846,626 filed Mar. 5, 1992, now U.S. Pat. No. 5,212,139.

BACKGROUND OF THE INVENTION

The present invention relates to a process for converting methane gases to high hydrocarbons, a catalyst for use in such processes and a method for preparing such a catalyst.

Methods for conversion of methane to high hydrocarbons are typically carried out using metal-based catalysts. Among the known conversion processes, catalysts based on manganese, magnesium and lead using alkali metal promoters have given good results in synthesis of methane to obtain ethane/ethylene type products. Among these catalysts used in such processes, catalysts based upon oxides of manganese have been extensively studied and described.

U.S. Pat. No. 4,499,322 to Jones et al. discloses a process of methane conversion using an oxidative synthesizing agent containing a promoting amount of alkali metal and/or compounds thereof.

U.S. Pat. No. 4,547,608 discloses the use of a support material for a catalyst which comprises alkaline earth metal oxides and silicon oxides, alumina and mixtures thereof.

Published European Patent Application No. 0316075-A1 discloses a process for conversion of methane to higher hydrocarbons using a catalyst comprising manganese oxides which incorporate at least one of the elements tin, titanium, tungsten, tantalum, silicon, germanium, lead, phosphorus, arsenic, antimony, boron, gallium, indium, a lanthanide or an actinide. The method for preparation of this catalyst is disclosed as comprising the steps of calcining the manganese dioxide at 1000° C. for 16 hours to obtain $Mn_3O_4$, which is impregnated with a solution of sodium chloride and finally diluted with fines of silica.

Published European Patent Application No. 0365181-A1 discloses a process for preparation of a cogel catalyst for use in conversion of methane to higher hydrocarbons. The disclosed process involves the mixing of an aqueous solution of a soluble salt of an alkali or alkaline earth metal with a solution of a soluble compound of a metal thermally decomposable to a metal oxide. A solution in a hydroxylic solvent of a hydrolyzable silane is then added to this mixture, and this mixture is then maintained under such conditions that the mixture forms a cogel, while avoiding the formation of precipitates or particles. This cogel is then dried and calcined to obtain the desired catalyst.

While the above-described catalysts obtain satisfactory initial conversion rates of methane to higher hydrocarbons, this initial activity decreases rapidly during reaction time.

Accordingly, it is the principal object of the present invention to disclose a catalyst which possesses high conversion rates which do not rapidly decrease during reaction time, and a method for preparation of such a catalyst.

It is a further object of the present invention to provide a process for the conversion of methane to higher hydrocarbons which utilizes a catalyst prepared according to the present invention, to yield enhanced results in the conversion process.

Other aspects, objectives and advantages of the present invention will be apparent to those skilled in the art after a consideration of the accompanying detailed description of the invention and figures which are referred to therein.

SUMMARY OF THE INVENTION

The present invention relates to a catalyst for conversion of methane to higher hydrocarbons, comprising a support material selected from a group consisting of oxides of silicon, zirconium, magnesium and rhenium; a manganese catalytic agent supported on the support material; and an alkali metal promoter impregnated into the catalyst, wherein a surface atomic ratio of promoter to manganese is at least 5.

The present invention also relates to a method for preparation of a catalyst for the conversion of methane to higher hydrocarbons, comprising the steps of forming a mixture of a manganese aqueous solution and an oxidative agent aqueous solution in an inorganic oxide support material; varying a pH value of the mixture between acidic and basic values to obtain a precipitate of manganese oxide; drying the manganese oxide precipitate; impregnating the dried manganese oxide precipitate with a promoter to obtain an impregnated solid; drying the impregnated solid; and calcining the impregnated solid until a surface atomic ratio of promoter to manganese is at least 5.

The catalytic agent is preferably supplied in the form of an aqueous solution of manganese chloride. The oxidative agent is preferably a chlorate, hypochlorite, thiosulfate, or bromate of an alkali metal. The inorganic oxide support material is preferably selected from oxides of silicon, zirconium, or magnesium.

The promoter which is impregnated into the dried manganese oxide precipitate is preferably any alkali metal halide, and most preferably sodium chloride.

A process is also disclosed, according to the present invention, whereby the catalyst of the present invention is employed in the conversion of methane to higher hydrocarbons. This process comprises the steps of providing a methane gas; providing a catalyst based on manganese oxide and impregnated with a promoter, wherein a surface atomic ratio of promoter to manganese oxide is at least 5; and contacting the methane gas with the catalyst.

The improved stability of the catalyst prepared according to the disclosed method is believed to result from the high surface ratio of promoter to manganese which is more clearly set forth in the detailed description and examples to follow.

BRIEF DESCRIPTION OF THE DRAWINGS

A detailed description of the invention follows, with reference to the accompanying drawings, wherein:

FIG. 3 is a graph showing the selectivity of a catalyst prepared according to the present invention, as disclosed in Example 2 hereafter; and FIG. 4 is a graph showing the selectivity of a catalyst prepared according to the present invention, as disclosed in Example 3 hereafter.

DETAILED DESCRIPTION

Figure 1:
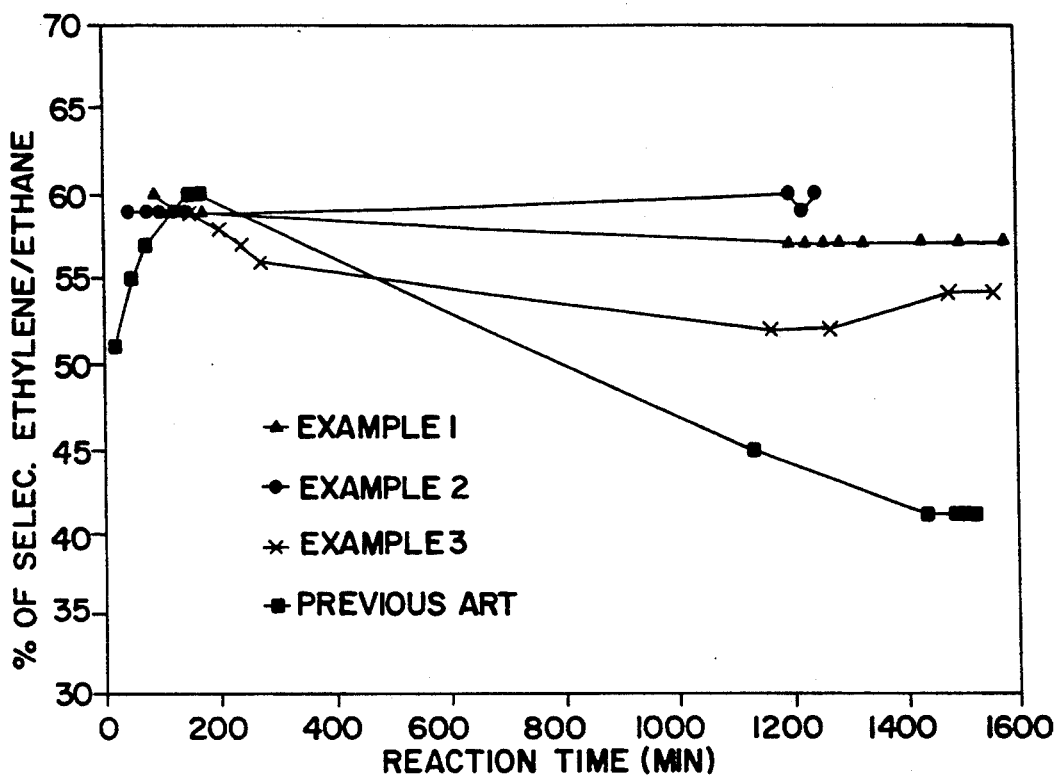
FIG. 1 is a graph showing the selectivity of catalysts prepared according to the present invention, as compared to a prior art catalyst.

The disclosed invention pertains to a catalyst for use in conversion of methane to higher hydrocarbons and a method for preparation of same.

In accordance with the invention, a mixture is made of a manganese aqueous solution and an oxidative agent aqueous solution in an inorganic oxide support material.

The catalytic agent aqueous solution is preferably an aqueous solution of manganese chloride.

The oxidative agent is preferably a chlorate, hypochlorite, thiosulfate, or bromate of an alkali metal. Most preferably, potassium chlorate is used as the oxidative agent contained in the oxidative agent aqueous solution.

The inorganic oxide support material is preferably based on oxides of silicon, zirconium, or magnesium. In an alternate embodiment of the invention, and preferably when silicon oxide is used as the support material, the inorganic oxide is calcined prior to its addition to the mixture of manganese and oxidative agent.

The mixture formed of the above components is then treated to obtain a manganese oxide precipitate. This precipitate is preferably obtained by varying a pH value of the mixture between acidic and basic values until the desired manganese oxide precipitate is obtained. The proper manipulation of the pH of the mixture can be obtained through the addition of, for example, ammonium hydroxide to obtain a basic value pH, and by the addition of, for example, nitric acid to obtain the desired acidic values. During the additions of these pH manipulating agents, the mixture should be continuously stirred.

Once a desired amount of solid manganese oxide precipitate is obtained, the solid is evaporated to eliminate water surplus, and then dried in a furnace, preferably at a temperature of 100° C. for a period of 4 hours.

This solid is then impregnated with a promoter to improve the catalytic activity of the obtained material. Promoters which are particularly suitable to the present invention include those selected from a group of alkali metal halides, and most preferably, sodium chloride. This promoter is impregnated into the solid in a solution, using techniques which are known in the art. The impregnated solid is then dried, preferably at a temperature in the range of 100°–140° C., and the dried solid is then calcined at a temperature in the range of 300°–1000° C., and more preferably in the range of 600°–800° C.

For reasons that are not known, the resulting catalyst, when subjected to suitable testing, exhibits a surface atomic ratio of promoter to manganese which is higher than those of catalysts prepared according to methods of the prior art. Further, catalysts obtained according to the method of the present invention exhibit a greatly enhanced stability of conversion over periods of reaction time.

According to an alternate embodiment of the invention, and most preferably in the method wherein silica is used as the support material, the precipitated manganese oxide may be calcined prior to its impregnation at a temperature in the range of 900°–1200° C., and most preferably at a temperature of 1000° C.

The aforementioned surface ratio of promoter to catalytic agent is preferably measured by using X-ray photoelectron spectroscopy (XPS). Signals generated by such spectroscopy allow the determination and estimation of the amount of materials which are present at the surface of the catalyst, and which are, accordingly, responsible for catalytic activities possessed by the catalyst. XPS results in excitement of the atoms of the material being measured. The energy spectrum of the electrons emitted by photo emission are then measured. The kinetic energy with which the electrons are liberated is such that only those that are near the surface of the catalyst (within a distance of less than 100 angstroms) escape from the material to be detected. Thus, this method gives an accurate measure of the composition of materials at the surface of the catalyst.

As will be more clearly demonstrated in the following examples, catalysts prepared according to the prior art processes possess a relatively low ratio of promoter to manganese at the surface, as measured by XPS techniques, and the ratio of the prior art catalysts decreases with use. Also as clearly shown in the following examples, however, catalysts prepared according to the present invention exhibit ratios of promoter to manganese which are higher than those exhibited by prior art catalysts, and generally in the range of at least 5, and these ratios either increase, or remain relatively constant, over periods of use.

Accordingly, a method is described whereby catalysts can be produced having high ratios of promoter to catalytic agent located at the surface of the catalyst, which catalysts exhibit great stability in conversion rates over extended periods of use.

The catalyst produced according to the invention may preferably be used in a process of conversion of methane to higher hydrocarbons, wherein the methane to be converted may be either pure methane or a methane-containing gas. Thus, the methane may be mixed with a molecular oxygen containing oxidant gas such as oxygen, air or an air/oxygen mixture. In this instance, it is preferable to employ methane and oxygen in a ratio by volume in the range of 2–10:1 of methane to oxygen.

Inert diluents may also be present in the methane to be treated, such as argon, helium and nitrogen.

The treatment process comprises the steps of providing the desired methane or methane gas mixture, preparing a catalyst having a surface ratio of promoter to catalytic agent of at least 5, according to the aforesaid method, and contacting the methane gas with the catalyst at a temperature in the range of 500°–1000° C., and more preferably in the range of 600°–900° C. The gas is preferably supplied to the catalyst at a space velocity measured at standard temperature and pressure in the range of 100–100,000 $h^{-1}$, $h^{-1}$. This process is also preferably carried out in a continuous manner.

The conversion rates obtained by this process are demonstrated more clearly in the examples which follow.

EXAMPLE NO. 1

A starting solution of $MnCl_3 4H_2O$ (14.43 g in 20 ml of $H_2O$) and $KClO_3$ (4 g in 40 ml of $H_2O$) was added to 19 g of silica which was previously calcined (1000° C., 16 h) and suspended in 40 ml of $H_2O$, at environmental temperature and maintaining continuous stirring.

$NH_4OH$ was introduced into the mixture to obtain a basic solution. $HNO_3$ was then added, during continuous stirring, to obtain an acidic solution. As a result of the manipulation of the pH of the solution, a solid manganese oxide precipitate was obtained. This solid was evaporated to eliminate water surplus, and then dried in a furnace at 100° C. for a period of 4 hours. The dried solid was then calcined at a temperature of 1000° C. for a period of 16 h. This calcined solid was then impregnated with a solution of sodium chloride (18 g in 80 ml of $H_2O$) during a period of 2 hours of constant stirring. The impregnated solid was then dried in a furnace at 100° C. for 4 hours, and calcined at 700° C. for 16 hours.

EXAMPLE NO. 2

A catalyst was prepared following the identical method as described in Example 1, but omitting the step of calcining the dried solid prior to the impregnation step.

EXAMPLE NO. 3

A catalyst was prepared in an identical procedure as that described in Example 1, except that the silicon oxide had not previously been calcined, and the dried solid was also not calcined prior to its impregnation.

EXAMPLE NO. 4

A catalyst was prepared using a procedure identical to that described in Example No. 3, but the support material was zirconium oxide.

EXAMPLE NO. 5

A catalyst was prepared following a procedure identical to that described in Example No. 3, except that the support material was magnesium oxide.

Table I contains the results obtained from evaluation of the catalysts prepared according to Examples 1-5 above, regarding their conversion of methane to ethylene/ethane products.

TABLE I

| Example | T (°C.) | % Conversion $CH_4$ | $O_2$ | % Selec. $C_2$ | % Yield $C_2$ | $C_2^=/C_2$ |
|---|---|---|---|---|---|---|
| 1 | 720 | 25 | 92 | 53 | 13 | 3.2 |
|   | 740 | 32 | 100 | 59 | 19 | 5.6 |
| 2 | 720 | 35 | 100 | 59 | 21 | 4.0 |
|   | 740 | 33 | 100 | 61 | 20 | 5.5 |
| 3 | 720 | 34 | 100 | 62 | 21 | 5.7 |
|   | 740 | 35 | 100 | 60 | 21 | 5.8 |
| 4 | 740 | 25 | 100 | 57 | 15 | 2.1 |
| 5 | 740 | 21 | 100 | 38 | 8 | 1.2 |

Operating conditions: 600 h[4], astmospheric pressure, 1 cc of catalyst. T (°C.) temperature of catalytic bed.

COMPARATIVE EXAMPLE

A catalyst was prepared according to the method disclosed in afore-described European Patent Application No. 0316075-A1. $MnO_2$ was calcined at 1000° C. for 16 hours in order to obtain $Mn_3O_4$, which was then impregnated with a solution of NaCl. This substance was then diluted with a finely divided silica. Table II below contains the results obtained for evaluation of this catalyst for the conversion of methane.

TABLE II

| Catalyst | T (°C.) | % Conversion | % Selec. | % Yield | $C_2^=/C_2$ |
|---|---|---|---|---|---|
| $NaCl/Mn_3O_4/SiO_2$ | 720 | 29 | 59 | 17 | 3.4 |

Operating conditions: 1200 h[4], $CH_4/O_2$ = 4, atmospheric pressure, 5 cc of catalyst. T (°C.) = temperature of catalytic bed.

The catalyst prepared according to the teachings of the prior art, as well as the catalysts prepared in accordance with Examples 1-5 above, were then tested with X ray photoelectron spectroscopy (XPS) in order to evaluate the ratio of promoter to catalytic agent at the surface of these materials. The studies were carried out using a Leybold LHS-10 surface analysis apparatus using a radiation energy of 1253.6 eV, provided through a magnesium cathode with a power of 300 watts. The X-ray source was operated through a constant and sufficiently high power to assure high intensity of the signal without saturation of the detector (less than 120,000 cps).

The accumulated data were obtained by using a pulse counting system which is controlled by a computer, with intervals of energy of 0.2 eV. Energy sweeps were conducted until an adequate signal/noise ratio was reached. The procedure was conducted using a gap opening of 1 millimeter with a constant absolute resolution employing an energy step of 200 eV. The ratio of promoter to catalytic agent on the surface of the catalyst was determined by measuring the corrected signal area of the promoter to the catalytic agent.

Sensitivity factors were applied to this data to enable the surface atomic ratio to be evaluated.

The results obtained by the XPS testing of the catalyst prepared according to the invention in Examples 1-5 and of the prior art catalyst are shown in Table III hereinbelow, wherein % of Na and Mn are shown at the surface of the catalyst, as well as the ratio of Na to Mn.

TABLE III

| CATALYST | % Na | % Mn | Na/Mn |
|---|---|---|---|
| Previous art before reaction | 2.3 | 0.6 | 3.8 |
| Previous art after reaction | 3.0 | 1.1 | 2.7 |
| Example 1 before reaction | 10.6 | 1.9 | 5.6 |
| Example 1 after reaction | 15.6 | 1.3 | 12.0 |
| Example 2 before reaction | 6.6 | 1.3 | 5.1 |
| Example 3 after reaction | 14.2 | 2.4 | 5.9 |
| Example 3 before reaction | 7.3 | 1.1 | 6.6 |
| Example 3 after reaction | 6.1 | 1.1 | 5.5 |
| Example 4 before reaction | 12.7 | 2.4 | 5.3 |
| Example 4 after reaction | 14.0 | 2.5 | 5.6 |
| Example 5 before reaction | 12.4 | 2.3 | 5.4 |
| Example 5 after reaction | 12.2 | 2.4 | 5.1 |

The percentage of Na located at the surface of these catalysts was also evaluated per the following table and equation:

TABLE III A

| Catalyst | Bulk atomic percent of Na | Surface atomic percent of Na | Surface* Enrichment |
|---|---|---|---|
| Previous Art | 20 | 2.3 | 11.5 |
| Our method | 44 | 6.6–12.7 | 15–29 |

*Enrichment of the surface related to the bulk calculated as:
$$\frac{\text{Surface atomic \% of Na}}{\text{Bulk atomic \% of Na}} \times 100$$

As can be seen, the disclosed method also results in a larger percentage of total Na being deposited on the surface of the catalyst than in the prior art.

The catalysts prepared according to the procedure of Examples 1, 2 and 3 above were tested for their conversion of methane to higher hydrocarbons. 1 cc of each catalyst was introduced in a quartz reactor of 20 cm length and 5 mm diameter. The reactor was brought to a temperature in the range of 720°–740° C. A methane/oxygen mixture at a ratio of methane to oxygen of 4:1 was contacted with the catalyst at a space velocity of 600 h[−1] and at atmospheric pressure. These operating conditions were maintained constant for all tests.

The results for the catalyst according to Example 1 are indicated below in Table IV.

TABLE IV

| t (min) | Example No. 1 | | | | |
|---|---|---|---|---|---|
| | % Conversion | | % Sel. $C_2$ | % Yield $C_2$ | $C_2^=/C_2$ |
| | $CH_4$ | $O_2$ | | | |
| 90 | 34 | 99 | 60 | 20 | 5.4 |
| 126 | 34 | 99 | 59 | 20 | 5.3 |
| 153 | 33 | 99 | 59 | 19 | 5.2 |
| 172 | 33 | 99 | 57 | 19 | 5.2 |
| 1200 | 32 | 99 | 57 | 18 | 4.7 |
| 1229 | 32 | 99 | 57 | 18 | 4.7 |
| 1263 | 32 | 99 | 57 | 18 | 4.7 |
| 1291 | 32 | 99 | 57 | 18 | 4.6 |
| 1359 | 31 | 99 | 57 | 18 | 4.6 |
| 1499 | 31 | 99 | 57 | 18 | 4.5 |
| 1579 | 31 | 99 | 57 | 18 | 4.5 |
| 2573 | 29 | 90 | 57 | 16 | 4.0 |
| 2611 | 28 | 90 | 57 | 16 | 4.0 |
| 2635 | 28 | 89 | 57 | 16 | 3.9 |

The results for the catalyst of Example 2 are incorporated below in Table V.

TABLE V

| t (min) | Example No. 2 | | | | |
|---|---|---|---|---|---|
| | % Conversion | | % Sel. $C_2$ | % Yield $C_2$ | $C_2^=/C_2$ |
| | $CH_4$ | $O_2$ | | | |
| 45 | 35 | 100 | 59 | 21 | 4.0 |
| 75 | 35 | 100 | 59 | 21 | 3.9 |
| 100 | 35 | 100 | 51 | 21 | 3.9 |
| 135 | 35 | 100 | 59 | 21 | 4.0 |
| 1200 | 30 | 77 | 60 | 18 | 2.8 |
| 1223 | 30 | 79 | 60 | 18 | 2.9 |
| 1246 | 30 | 78 | 60 | 18 | 2.9 |

The results of the testing of the catalyst according to Example 3 are contained in Table VI.

TABLE VI

| t (min) | Example No. 3 | | | | |
|---|---|---|---|---|---|
| | % Conversion | | % Sel. $C_2$ | % Yield $C_2$ | $C_2^=/C_2$ |
| | $CH_4$ | $O_2$ | | | |
| 100 | 31 | 100 | 59 | 18 | 4.7 |
| 145 | 31 | 100 | 59 | 18 | 4.7 |
| 200 | 31 | 100 | 58 | 18 | 4.8 |
| 240 | 30 | 96 | 57 | 17 | 4.7 |
| 270 | 31 | 95 | 56 | 18 | 4.5 |
| 1170 | 31 | 92 | 52 | 16 | 3.4 |
| 1270 | 29 | 92 | 52 | 16 | 3.4 |
| 1480 | 29 | 92 | 54 | 16 | 3.4 |
| 1560 | 28 | 91 | 54 | 15 | 3.3 |
| 1610 | 28 | 92 | 55 | 15 | 3.3 |

With reference to FIG. 1, the ethylene/ethane selectivity of the prior art catalyst and the catalysts prepared according to Examples 1-3 are graphically illustrated. As can be observed, catalysts prepared according to the present invention reach their maximum selectivity at the beginning of the reaction and then, unlike the prior art catalyst, maintain a substantially stable activity during the entire reaction time.

Figure 2:
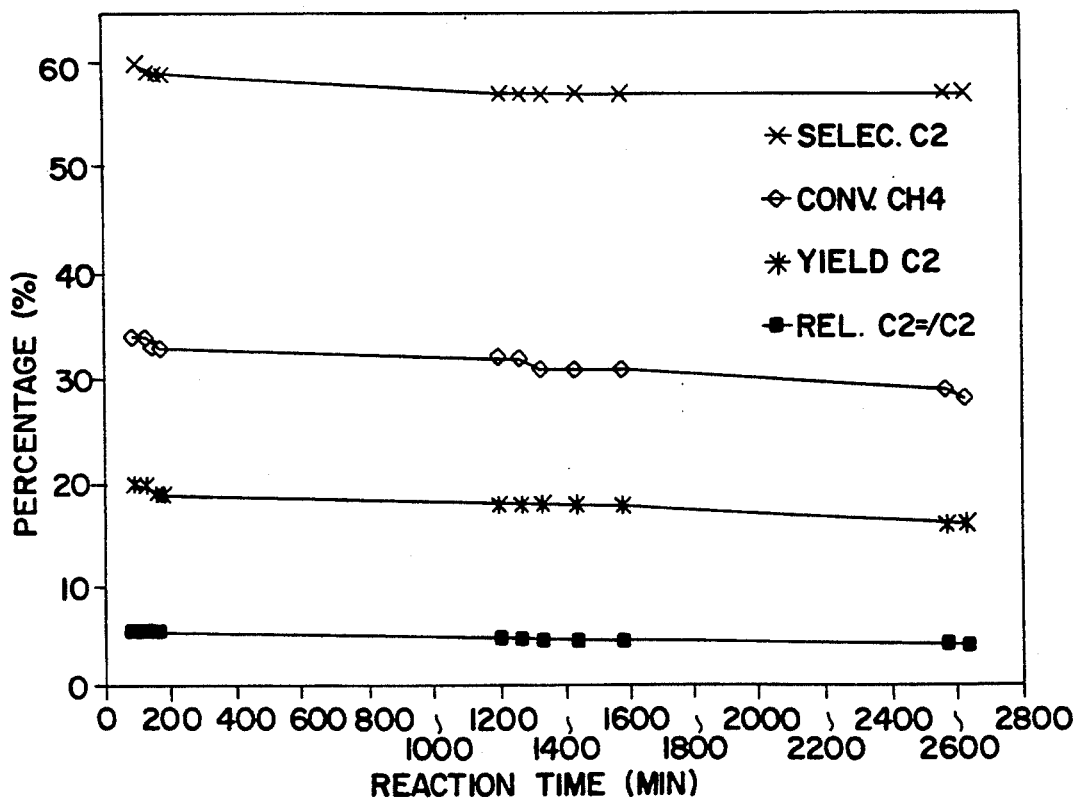
FIG. 2 is a graph showing the selectivity of a catalyst prepared according to the present invention, as disclosed in Example 1 hereafter.

With reference to FIGS. 2-4, the activity of the catalyst according to Examples 1-3 respectively, is graphically depicted. The figures show selectivity to ethane/ethylene type products. As can be seen, high catalytic stability relative to the prior art catalyst is clearly achieved.

It is also observed that the highest apparent stability is that exhibited by the catalyst of Example 1, which also exhibited the highest ratio of promoter to catalytic agent. A correlation is therefore indicated between the ratio and catalytic stability.

The catalyst of the present invention is also useful in Oxidative Dehydrogenation Processes. The process comprises contacting oxygen or oxygen containing gas which also contains one or more dehydrogenatable hydrocarbons such as ethane, propane, cyclo alkanes or other alkanes, with a catalyst according to the present invention.

The dehydrogenated product obtained by such a process depends upon the feedstock selected, for example, alkanes may be treated to obtain olefins, diolefins, alkynes, etc.

Operating temperatures for such dehydrogenation procedures are generally in a range of 500°-1000° C., preferably 600°-900° C. Space velocity of the process at standard temperature and pressure is generally in a range of from 100-100,000h$^{-1}$, and preferably about 300-5000h$^{-1}$.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A process for converting methane to higher hydrocarbons, comprising the steps of:
   providing a methane gas;
   providing a catalyst comprising a support material selected from the group consisting of oxides of silicon, zirconium and magnesium; a manganese catalytic agent supported on the support material; and an alkali metal promoter impregnated into the catalyst; wherein a surface atomic ratio of promoter to manganese is at least 5; and
   contacting the methane gas with the catalyst at effective methane conversion conditions.

2. A process according to claim 1, wherein the contacting step is carried out at a temperature of between about 600° C. to 900° C.

3. A process according to claim 1, wherein the step of providing the methane gas comprises providing a mixture of methane with oxygen wherein a ratio by volume of methane to oxygen is between about 2:1 to 10:1.

4. A process for dehydrogenating a hydrocarbon, comprising the steps of:
   providing a feedstock including oxygen and dehydrogenatable hydrocarbon;
   providing a catalyst comprising a support material selected from the group consisting of oxides of silicon, zirconium and magnesium; a manganese catalytic agent supported on the support material; and an alkali metal promoter impregnated into the catalyst; wherein a surface atomic ratio of promoter to manganese is at least 5; and
   contacting the feedstock with the catalyst at effective dehydrogenation conditions.

5. A process according to claim 4, wherein the contacting step is carried out at a temperature of between about 600° C. to 900° C.

* * * * *